(12) United States Patent
Kubo

(10) Patent No.: US 7,964,071 B2
(45) Date of Patent: Jun. 21, 2011

(54) DEVICE WITH π-CONJUGATED METAL COMPLEX IMMOBILIZED SUBSTRATE IN AQUEOUS ELECTROLYTE

(75) Inventor: Wataru Kubo, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 406 days.

(21) Appl. No.: 12/168,599

(22) Filed: Jul. 7, 2008

(65) Prior Publication Data
US 2009/0026071 A1    Jan. 29, 2009

(30) Foreign Application Priority Data

Jul. 23, 2007 (JP) ................................ 2007-190705

(51) Int. Cl.
*G01N 27/28* (2006.01)
(52) U.S. Cl. .................................................... 204/403.1
(58) Field of Classification Search ................ 204/403.1
See application file for complete search history.

(56) References Cited

U.S. PATENT DOCUMENTS

| | | | | |
|---|---|---|---|---|
| 5,160,418 | A * | 11/1992 | Mullen | 204/403.14 |
| 7,687,186 | B2 * | 3/2010 | Kubo et al. | 429/401 |
| 2005/0095466 | A1 * | 5/2005 | Minteer et al. | 429/12 |
| 2006/0278868 | A1 * | 12/2006 | Matsui | 257/40 |

OTHER PUBLICATIONS

R. D. Shannon, "Revised Effective Ionic Radii and Systematic Studies of Interatomic Distances in Halides and Chaleogenides," A32 Acta Cryst. 751-67 (1976).
R. Wachter et al., "Properties of Dilute Electrolyte Solutions from Calorimetric Measurements," 53 Pure & Appl. Chem. 1301-12 (1981).
Norman E. Heimer et al., "13C NMR Relaxation Rates in the Ionic Liquid 1-Ethyl-3-methylimidazolium Butanesulfonate," 110 J. Phys. Chem. A 868-74 (2006).
Katsuhiko Kanaizuka et al., "Stepwise Preparation of Linear π-Conjugated Bis(terpyridine)metal Polymer Chains at Gold Surface," 34(4) Chemistry Letters 534-35 (Mar. 2005).

* cited by examiner

*Primary Examiner* — Bruce F Bell
(74) *Attorney, Agent, or Firm* — Fitzpatrick, Cella, Harper & Scinto

(57) ABSTRACT

A π-conjugated metal complex immobilized substrate, in which π-conjugated metal complex molecules are connected to a substrate via a π-conjugated molecular structure, is adapted for observing an electron transfer (redox reaction) of the π-conjugated metal complex molecules in aqueous electrolytes. An electrochemical device including this π-conjugated metal complex immobilized substrate and an aqueous electrolyte with cations having an ion radius of r (m) that is not less than a radius of a sphere inscribed in a clearance formed between the π-conjugated metal complex molecules. The device utilizes an electron transfer (redox reaction) of the π-conjugated metal complex molecules in the aqueous electrolyte.

2 Claims, 8 Drawing Sheets

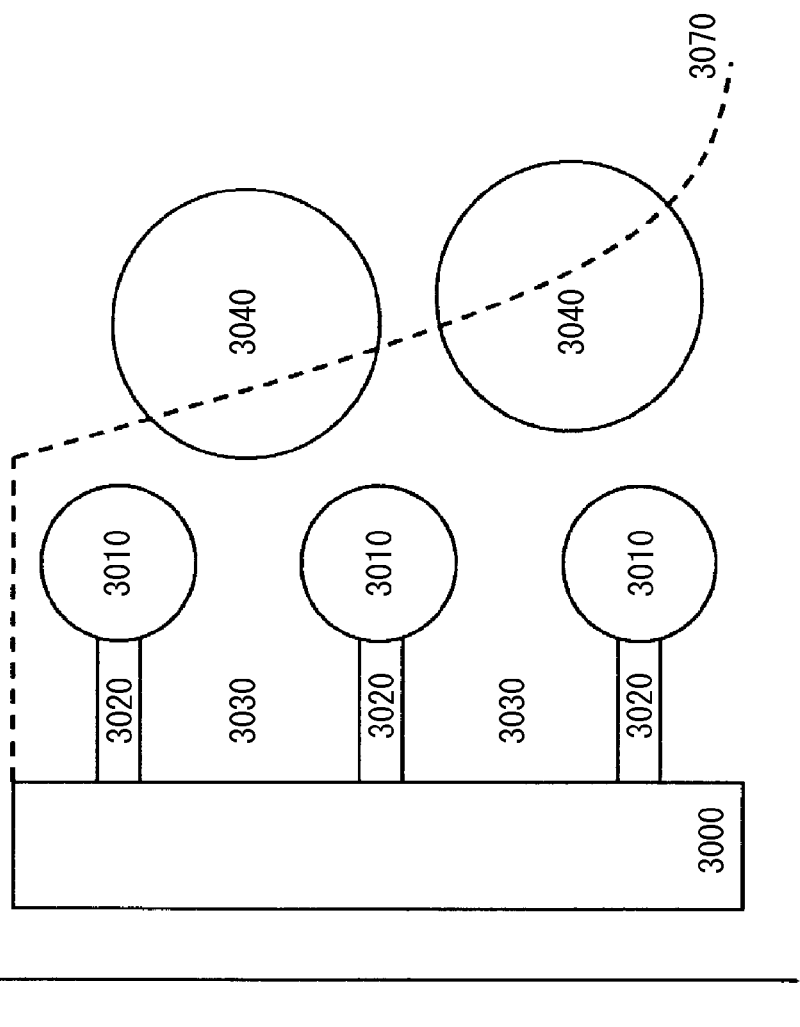
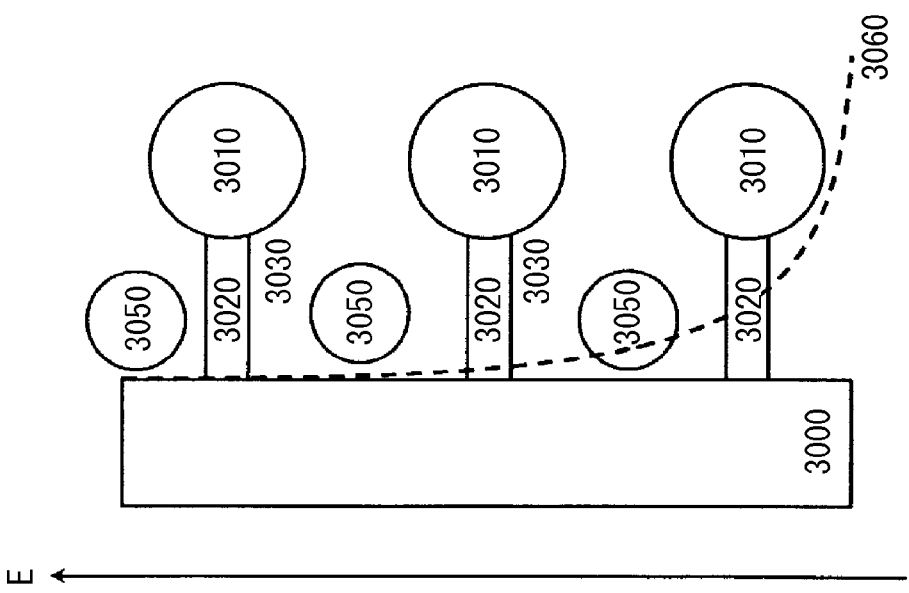

DEVICE WITH π-CONJUGATED METAL COMPLEX IMMOBILIZED SUBSTRATE IN AQUEOUS ELECTROLYTE

BACKGROUND OF THE INVENTION

1. Field of the Invention

The present invention relates to an electrochemical device with a π-conjugated metal complex immobilized substrate in an aqueous electrolyte.

2. Description of the Related Art

π-Conjugated metal complex immobilized substrates, in which π-conjugated metal complex molecules are immobilized on a substrate, have attracted attention, for example, as molecular wire materials in the field of molecular electronics. Among such substrates, π-conjugated metal complex immobilized substrates in which π-conjugated metal complex molecules are connected to a substrate via a π-conjugated molecular structure employ a high electron transfer ability of π-conjugated molecular structures and enable a high-speed electron transfer between the π-conjugated metal complex molecules and the substrates due to a redox reaction of the π-conjugated metal complex molecules. Redox behavior of a cobalt terpyridine complex in $CH_2Cl_2$ using a π-conjugated metal complex immobilized substrate, in which the cobalt terpyridine complex is immobilized on a substrate via azobenzene having a π-conjugated molecular structure, has been reported (Katsuhiko Kanaizuka, Masaki Murata, Yoshihiko Nishimori, Ichiro Mori, Kazuyuki Nishio, Hideki Masuda, Hiroshi Nishihara: Chem. Lett. 2005, 34, 534-535).

When the π-conjugated metal complex immobilized substrate, in which a connection to the substrate is performed via the π-conjugated molecular structure, is used in an electrochemical device together with a biological material, it is necessary to be able to observe the electron transfer in an aqueous electrolyte in order to preserve the structure and functions of the biological material. However, such an observation is difficult to perform.

SUMMARY OF THE INVENTION

The present invention provides an electrochemical device in which the electron transfer (redox reaction) of a π-conjugated metal complex molecules immobilized on a conductive substrate can be observed in an aqueous electrolyte.

In particular, the present invention provides an electrochemical device comprising a π-conjugated metal complex immobilized substrate in which π-conjugated metal complex molecules are immobilized on a conductive substrate directly or via a π-conjugated molecular structure and an aqueous electrolyte comprising cations with an ion radius of r (m) that is not smaller than a radius of a sphere inscribed in a clearance formed between the π-conjugated metal complex molecules (r≧A, where A (m) is the radius of the inscribed sphere). The device utilizes an electron transfer (redox reaction) of the π-conjugated metal complex molecules in the aqueous electrolyte.

The radius of a sphere inscribed in the clearance (A) is represented by the following Equation (1):

$$A = \frac{1}{\sqrt{2 \times 10^4 G N_A}} - R. \quad (1)$$

In Equation (1), G is an adsorption density (mol cm$^{-2}$) of the π-conjugated metal complex molecules, $N_A$ is Avogadro's number, and R is a molecular radius (m) of the π-conjugated metal complex molecule.

The cation having the ion radius r may be derived from an organic compound.

Other features of the present invention will become apparent from the following description of the exemplary embodiments with reference to the attached drawings.

BRIEF DESCRIPTION OF THE DRAWINGS

FIGS. 3A and 3B are schematic representations of a complex molecule/substrate interface.

DESCRIPTION OF THE EMBODIMENTS

The present invention provides an electrochemical device in which the electron transfer (redox reaction) of a π-conjugated metal complex molecules immobilized on a conductive substrate can be observed in an aqueous electrolyte. This type of observation in an aqueous electrolyte has been difficult, if not impossible, to perform using conventional means. The inventors have investigated the reasons for these difficulties.

The arrangement of the complex on the substrate was derived from the adsorption density of π-conjugated metal complex molecules. First, the π-conjugated metal complex molecules were assumed to have a circular shape when viewed from the upper surface of the substrate. Then, a model was considered in which the π-conjugated metal complex molecules are arranged so that centers of the circles thereof are positioned in apexes of a square and so that the adjacent circles are in contact with each other. The arrangement model of the π-conjugated metal complex molecules on a substrate is shown in FIG. 1.

Figure 1:
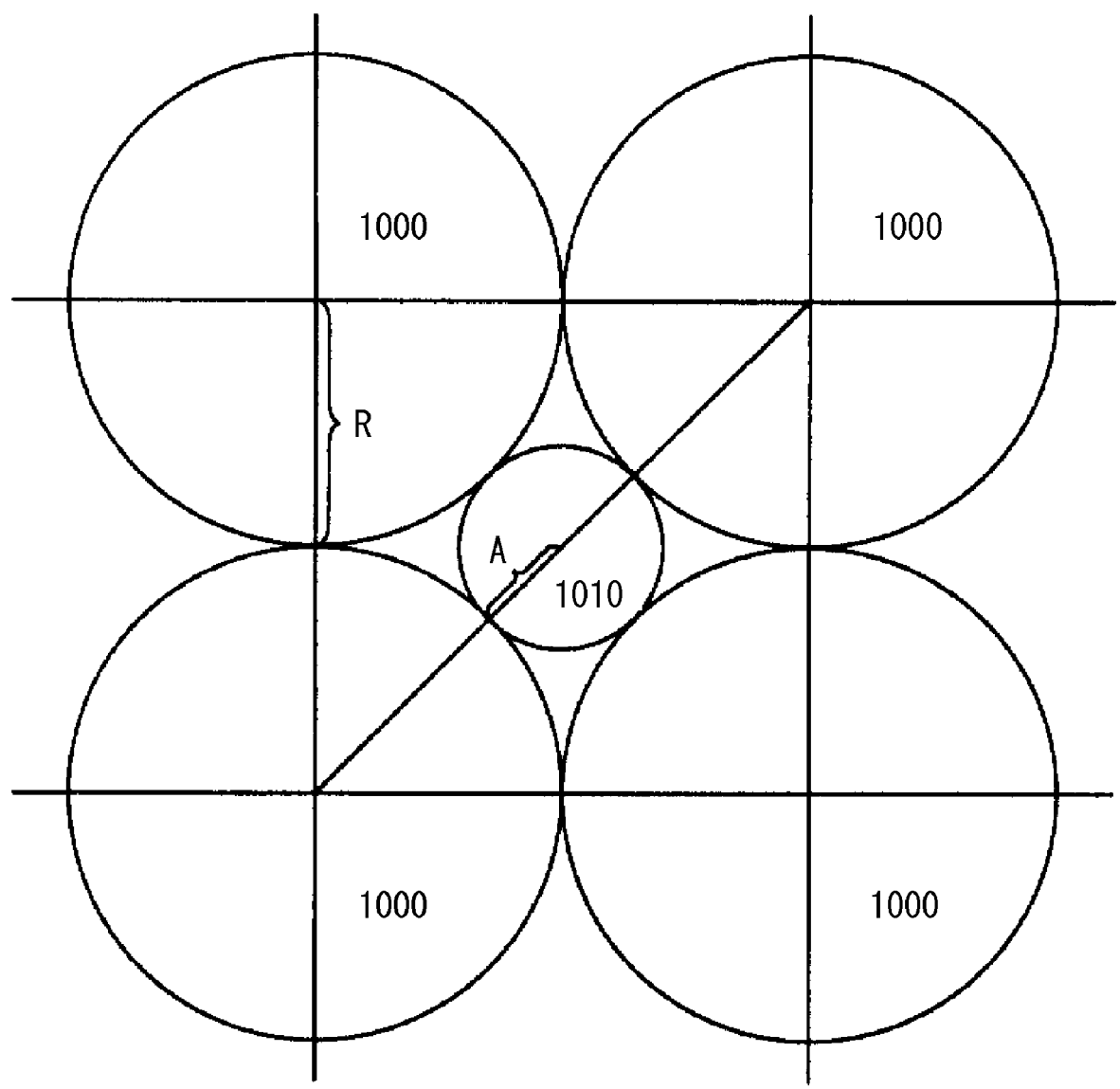
FIG. 1 shows the relationship between the molecular radius of a π-conjugated metal complex molecule immobilized on a substrate and the radius of a circle inscribed in the clearance formed between the π-conjugated metal complex molecules.

In FIG. 1, reference numeral 1000 denotes a circle (radius is taken as R(m)) that represents a π-conjugated metal complex molecule immobilized on the substrate. The circles are arranged so that their centers form a square. Assuming that cobalt terpyridine complexes (estimated complex radius is 0.58 nm) are arranged similar to the circles in the drawing, the calculated adsorption density will be 1.23×10$^{-10}$ mol cm$^{-2}$. This calculated value is approximately equal to the actually measured adsorption density (1.25×10$^{-10}$ mol cm$^{-2}$) when the cobalt terpyridine complexes are adsorbed to the limit adsorption amount on a glass substrate with a vapor-deposited gold surface. It was inferred therefrom that the π-conjugated metal complex molecules (cobalt terpyridine complexes) are so arranged that the centers thereof are positioned in the apexes of a square and that the adjacent π-conjugated metal complex molecules are in contact with each other.

Further, in FIG. 1, the radius A of a sphere 1010 (radius A (m)) inscribed in the clearance formed between the π-conjugated metal complex molecules can be represented by Equation (1) by using the radius R (m) of a π-conjugated metal complex molecule and the adsorption density G (mol cm$^{-2}$) of the complex.

Here, a case will be considered in which a cobalt terpyridine complex (estimated complex radius R is 0.58 nm) is used as a π-conjugated metal complex molecule and the adsorption density G of the cobalt terpyridine complex is $1.25 \times 10^{-10}$ mol cm$^{-2}$. In this case, the radius A of a sphere inscribed in the clearance formed between the cobalt terpyridine complex molecules can be calculated as 0.239 nm from Equation (1):

$$A = \frac{1}{\sqrt{2 \times 10^4 G N_A}} - R. \tag{1}$$

In Equation (1), G represents the adsorption density (mol cm$^{-2}$) of π-conjugated metal complex molecules, $N_A$ is Avogadro's number, and R is a molecular radius (m) of the π-conjugated metal complex molecule. Due to their high solubility and availability, cations having a comparatively small ion radius, for example, sodium ions (ion radius 0.102 nm), are typically used as cations in aqueous electrolytes. Assuming that a sodium ion (ion radius 0.102 nm), which is a cation having an ion radius less than the clearance (radius 0.239 nm) formed between the π-conjugated metal complex molecules (cobalt terpyridine complex), penetrates between the π-conjugated metal complex molecules and substrate, the electric potential that has to be applied to the π-conjugated metal complex molecules is screened and the electron transfer (redox reaction) cannot be observed. The inventors thus determined that the observations of the electron transfer (redox reaction) can be performed when an electrolyte that is used is composed of cations having an ion radius equal to or larger than the radius of a sphere inscribed in the clearance formed between the π-conjugated metal complex molecules. Thus, when the ion radius r of an electrolyte cation is equal to or larger than the radius A of the sphere inscribed in the clearance formed between the π-conjugated metal complex molecules (r≧A), the cation can be prevented from penetrating between the π-conjugated metal complex molecules and the substrate. As a result, the electric potential applied to the π-conjugated metal complex molecules is not screened and, therefore, the electron transfer (redox reaction) can be observed.

In view of the above, the higher is the adsorption density of the π-conjugated metal complex molecules, the smaller is the radius of the cations in the electrolyte that can allow the electron transfer (redox reaction) of π-conjugated metal complex molecules to be observed. As described above, when a cobalt terpyridine complex (estimated complex radius is 0.58 nm) with a small complex radius is used as the π-conjugated metal complex molecule, the adsorption density of the cobalt terpyridine complex in the above-described model is $1.23 \times 10^{-10}$ mol cm$^{-2}$. The ion radius of the electrolyte cation that can be used in this case is equal to or more than 0.239 nm. However, it is difficult to expect the adsorption density of a π-conjugated metal complex molecule to be equal to or higher than the adsorption density of a π-conjugated molecular structure that connects the π-conjugated metal complex molecules and substrate. For example, the adsorption density of an alkanethiol alone is $7.7 \times 10^{-10}$ mol cm$^{-2}$.

A supporting salt added to an electrolyte is used to impart the electrolyte with necessary conductivity and to enhance the electrochemical reaction. The conductivity is proportional to the mobility of electrolyte ions. Further, the mobility of electrolyte ions is generally inversely proportional to the electrolyte ion radius. Therefore, increasing the ion radius of the electrolyte ions decreases conductivity. However, taking into consideration the functions inherent to supporting salts, although these salts are designed to increase the electrolyte ion radius, decreasing the conductivity is impractical. Increasing the electrolyte concentration can be considered as a means for compensating for this decrease in conductivity. However, using a high-concentration electrolyte is impractical from the standpoint of solubility and the cost of the electrolyte. Therefore, the upper limit of the ion radius of the electrolyte cations is preferably capped by a tenfold radius of the typically used electrolyte cations. When a sodium ion that is typically used is an electrolyte cation, a radius equal to or less than 1.02 nm, which is not more than ten times the radius of the sodium ion, is the ion radius of the electrolyte cations that can be used in this case. When the aforementioned cobalt terpyridine complex (complex adsorption density is taken as $1.23 \times 10^{-10}$ mol cm$^{-2}$) is used, the ion radius of the electrolyte cation that can be used is from 0.239 nm to 1.02 nm.

Figure 2:
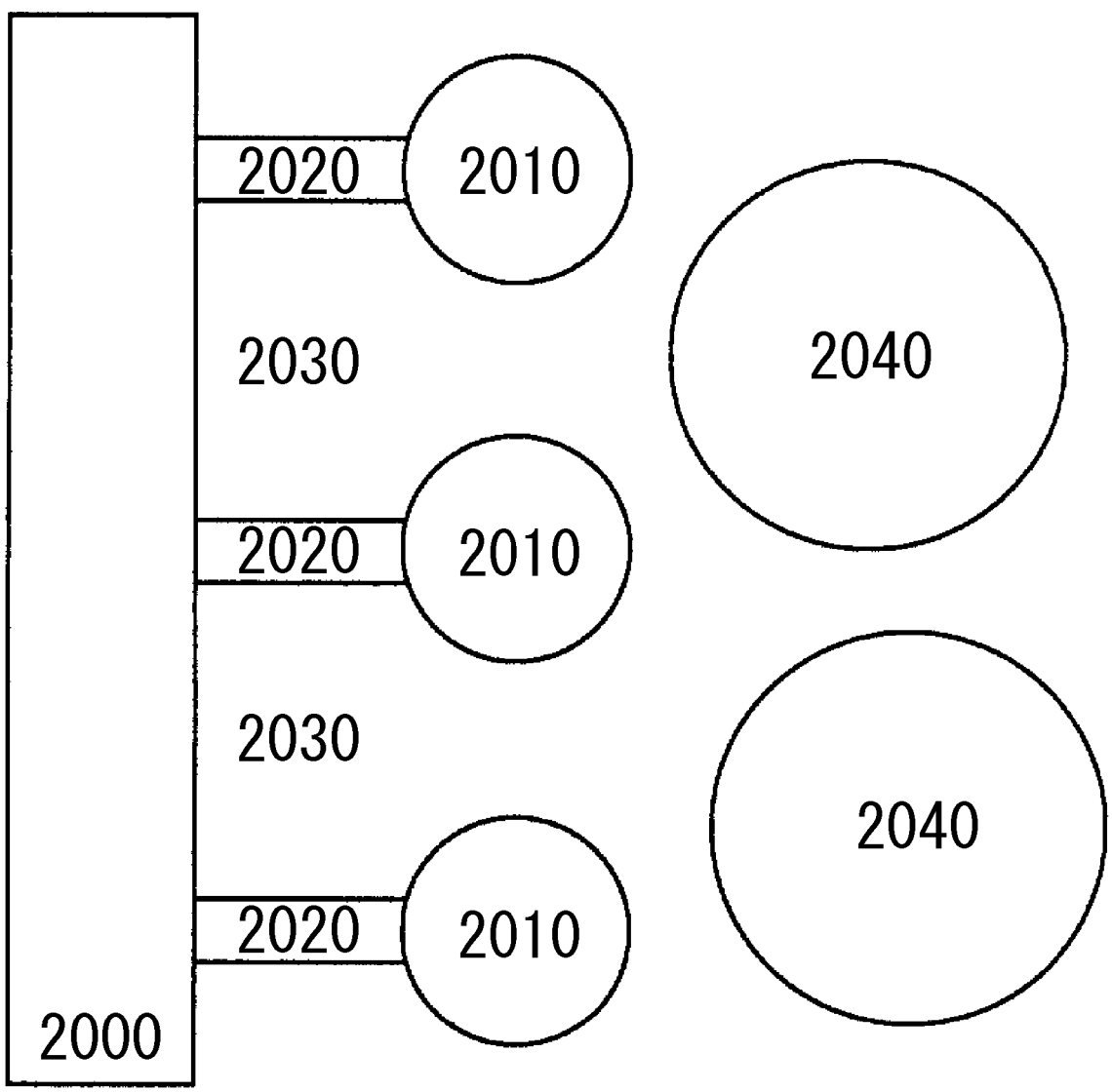
FIG. 2 is a conceptual view of a π-conjugated metal complex immobilized substrate.

FIG. 2 shows a conceptual diagram of the π-conjugated metal complex immobilized substrate in accordance with the present invention. In FIG. 2, reference numeral 2000 represents a substrate, 2010—a π-conjugated metal complex molecule, 2020—a π-conjugated molecular structure connecting the π-conjugated metal complex molecule and substrate, and 2030—an aqueous electrolyte (when the π-conjugated metal complex molecule is directly connected to and immobilized on the substrate, the π-conjugated molecular structure 2020 is unnecessary). Further, reference numeral 2040 represents an electrolyte cation having a large ion radius.

In accordance with the present invention, a cation is prevented from penetrating between the π-conjugated metal complex molecule connected to a substrate directly or via a π-conjugated molecular structure and the substrate by using an aqueous electrolyte cation having an ion radius equal to or larger than a clearance formed between the π-conjugated metal complex molecules. Screening of the electric potential applied to the π-conjugated metal complex is thereby prevented. As a result, the electron transfer (redox reaction) of the π-conjugated metal complex molecule immobilized on the conductive substrate can be observed in the aqueous electrolyte.

The π-conjugated metal complex immobilized substrate used in accordance with the present invention is characterized by using π-conjugated metal complex molecules immobilized on the substrate. Here, a π-conjugated metal complex molecule is a complex molecule in which a complex skeleton is configured by a central metal of the complex and at least one π-conjugated ligand.

In the π-conjugated metal complex molecule used in accordance with the present invention, the π-conjugated ligand is directly immobilized on the substrate via a functional group directly bonded to the π-conjugated ligand, or the π-conjugated ligand is immobilized on the substrate via a π-conjugated molecular structure and a functional group directly bonded to the π-conjugated molecular structure. Specific examples include a configuration in which a terpyridine complex is bonded to gold on the substrate via a thiol group and a configuration in which a terpyridine complex is bonded to the gold via a phenyl group and a thiol group bonded to the phenyl group.

The π-conjugated metal complex molecule may be a polynuclear complex having a plurality of metal elements or a mononuclear complex having one metal element. Also, metals contained in one π-conjugated metal complex molecule may be of more than one kind. In accordance with the present invention, transition metals are preferably used as the metal elements constituting the π-conjugated metal complex molecule. Specific examples of such elements include Os, Fe, Ru, Co, Cu, Ni, V, Mo, Cr, Mn, Pt, Rh, Pd, and Ir.

Any compound that has sufficient chemical stability and the ability to be oriented under conditions at which the electrode is used in an aqueous electrolyte and at which π-conjugation spreads over the molecular skeleton can be advantageously used as the π-conjugated ligand in the π-conjugated metal complex molecule. The preferred examples include bipyridine, terpyridine, phenanthroline, porphyrin, phthalocyanine, and derivatives thereof. Bipyridine derivatives and terpyridine derivatives are particularly preferred.

A structure that is a π-conjugated molecule and has sufficient chemical stability and the ability to be oriented under conditions at which the electrode is used in an aqueous electrolyte can be advantageously used as the π-conjugated molecular structure connecting the π-conjugated metal complex molecule and the substrate. Specific examples include an acetylene bond, a benzene ring, a pyrrole ring, a thiophene ring, a pyridine ring, and a diazo bond. It is more preferable for 1 to 5 of acetylene bond, benzene ring, pyrrole ring, thiophene ring, pyridine ring, and diazo bond to be contained. Further, the π-conjugated metal complex molecule can be directly bonded to the substrate.

A means for immobilizing the π-conjugated metal complex molecule on a substrate are not particularly limited. Any immobilization method can be advantageously used, provided that a bond between the substrate and π-conjugated metal complex molecule can be obtained that has sufficient chemical and electrochemical stability under the conditions at which the electrode is used in aqueous electrolyte in the aqueous electrolyte. Further, it is also preferred that at least one of the π-conjugated ligands have a functional group for ensuring bonding with the electrode. Examples of suitable functional groups include a thiol group, a silicic acid group, a carboxyl group, a phosphoric acid group, an amino group, and a diazo group. A combination of a plurality of identical or different bonds for immobilization can be used to bond the substrate and a π-conjugated metal complex molecule in order to obtain target properties in the same electrode. Examples of such bonds include a metal-thiol bond, a silicon-silicon bond, a carbon-carbon bond, and a metal-phosphoric acid bond.

The adsorption density of the π-conjugated metal complex molecules on the substrate can be controlled, for example, via the concentration of the solution at the time the adsorption is performed, type of solvent, immersion time, presence of a co-adsorbent and the concentration thereof, weight ratio with the co-adsorbent, substrate selection, surface state of the substrate, selection of priming for the substrate, and surface treatment.

The adsorption density of the π-conjugated metal complex molecules on the substrate can be estimated by the amount of the electric charge derived from the complex during electrochemical measurements, such as cyclic voltammetry and chronoamperometry. Alternatively, for example, when the adsorption proceeds via a thiol group, the adsorption density can be estimated by linear sweep voltammetry toward a negative potential, a quartz oscillator microweighing method, and ellipsometry under the conditions of a basic aqueous solution. Further, the radius of the π-conjugated metal complex molecule can be evaluated by calculations using reference documents and molecular modeling software as a radius of a circle when the π-conjugated metal complex molecule immobilized on the substrate is considered as a circle when viewed from the upper surface of the substrate.

A method for measuring the redox charge amount of the complex metal by using cyclic voltammogram is described below as a specific example of a method for evaluating the adsorption amount. Thus, cyclic voltammetry measurements are performed by using the prepared π-conjugated metal complex immobilized substrate as a working electrode, using a reference electrode, and using platinum as the counter electrode. The respective electrodes are connected to a potentiostat and measurements are conducted at a scan rate of 100 $mVs^{-1}$ in a potential range including a potential region in which the central metal of the π-conjugated metal complex molecules is oxidized and reduced (for example, when the complex metal is Co (II/III), 0.4 to −0.4 V vs. Ag/Ag$^+$). For example, a 0.1M acetonitrile solution (subjected to nitrogen bubbling) of tetrabutylammonium hexafluorophosphate is used as the electrolytic solution. The amount of the charge at the peak of the observed voltammogram (for example, when the complex metal is Co (II/III), close to 0V vs. Ag/Ag$^+$) is measured. The adsorption density G (mol cm$^{-2}$) can be represented by Equation (2) below via the measured charge quantity $Q_1$(C), Faraday constant F (Cmol$^{-1}$), and electrode surface area A (cm$^2$):

$$G = \frac{Q_1}{FA}. \quad (2)$$

Another specific example of a method for evaluating the adsorption amount is a method for measuring the amount of the electric charge during reduction and desorption of a thiol group of a complex molecule by using linear sweep voltammetry. Thus, linear sweep voltammetry measurements are performed by using the prepared π-conjugated metal complex immobilized substrate as a working electrode, using a reference electrode, and using platinum as the counter electrode. The respective electrodes are connected to a potentiostat and measurements are conducted at a scan rate of 50 $mVs^{-1}$ by using a strongly basic electrolyte solution (0.5 M aqueous KOH solution subjected to nitrogen bubbling) as the electrolytic solution. The amount of the charge at the peak of the observed voltammogram (for example, when the complex molecule is 4'-(4-mercaptophenyl)-2,2':6',2''-terpyridine, close to −1.1 V vs. Ag/AgCl) is measured. The adsorption density G (mol cm$^{-2}$) can be represented by Equation (3) below via the measured charge quantity $Q_2$(C), Faraday constant F (Cmol$^{-1}$), and electrode surface area A (cm$^2$):

$$G = \frac{2Q_2}{FA} \quad (3)$$

The substrate transfers the electric charge acquired in the electron transfer reaction of the π-conjugated metal complex molecules to an external circuit. The shape of the substrate is not particularly limited. For example, the substrate may be flat, curved, or spherical in shape. Materials that have high electrical conductivity and demonstrate sufficient electrochemical stability under conditions at which the electrode is used can be advantageously employed as the structural materials for the substrate. Examples of such structural materials include metals, conductive polymers, metal oxides, and carbon materials. Examples of preferred metals include metals of at least one kind selected from Au, Pt, Ag, Ni, Cr, Fe, Mo, Ti, Al, Cu, V, In, Ga, and W, and these metals may be used as alloys and/or in the form of a plated coating. Preferred conductive polymers include at least one compound selected from polyacetylenes, polyarylenes, polyarylenevinylenes, polyacenes polyarylacetylenes, polydiacetylenes, polynaphthalens, polypyrroles, polyanilines, polythiophenes, polythienylenevinylenes, polyazolenes, and polyisothianaphthenes. Preferred metal oxides contain an element of at least one kind selected from In, Sn, Zn, Ti, Al, Si, Zr, Nb, Mg, Ba, Mo, W, V, and Sr. Examples of carbon materials include graphite, carbon black, carbon nanotubes, carbon nanohorns, fullerene compounds, and derivatives thereof.

A method for preparing the π-conjugated metal complex molecules in accordance with the present invention is not particularly limited, and a method in which the separately synthesized π-conjugated metal complex molecules are bonded to the substrate or a method in which the complex is prepared on the substrate can be advantageously used. A method in which a π-conjugated ligand having a functional group that is bonded to a substrate and then a metal ion is coordinated is an example of a methods in which the complex is prepared on the substrate. A polynuclear complex can be prepared by repeating the operations of further coordinating the π-conjugated ligands with the center metal and coordinating the metal ion. The formation of the π-conjugated metal complex immobilized substrate can be confirmed by observing electric current induced by oxidation and reduction of the complex in electrochemical measurements, or by the increase in weight in quartz oscillator microweighing, by microscopic observations under an interatomic force microscope or the like, and also by an IR spectrum.

Water is the main component of the solvent constituting the aqueous electrolyte used in the device in accordance with the present invention. This means that the volume of the water as a starting material is 40% or more of the volume of the prepared electrolyte at room temperature. This value is set to prevent the modification of proteins and the chain in their functions when applications in combination with biological materials are considered. Further, an organic solvent or the like may be included to ensure solubility of the supporting salt used or the stability of substances present in the electrolyte. Glycerol is an example of such an organic solvent. Combinations of anions and cations with a large ion radius often constitute ionic liquids, and they may be also included as the solvent.

The supporting salt is used to impart the electrolyte with necessary conductivity and to enhance electrochemical reactions. Therefore, in order to impart the electrolyte with sufficient conductivity, the supporting salt must be sufficiently soluble in the solvent. In aqueous electrolytes, salts having cations with a comparatively small ion radius, such as alkali metals or alkaline earth metals, are most often used because of high solubility and availability thereof.

The inventors considered why the electron transfer (redox reaction) of π-conjugated metal complex molecules using a π-conjugated metal complex immobilized substrate is difficult to observe in aqueous electrolytes. They postulated that cations having a comparatively small ion radius that are typically used in aqueous solutions penetrate between the π-conjugated metal complex molecules and substrate and screen an electric potential that has to be applied to the π-conjugated metal complex molecules, thereby making it difficult to observe the electron movement (redox reaction). To verify this, an aqueous electrolyte was prepared by using cations having an ion radius equal to or larger than the radius of the sphere inscribed in the clearance formed between the π-conjugated metal complex molecules and the electron transfer (redox reaction) of the π-conjugated metal complex molecules was observed. With such a procedure, the electron transfer (redox reaction) of the π-conjugated metal complex molecules could be observed.

FIG. 3A is a schematic representation of a complex molecule/substrate interface when cations having an ion radius that is less than that of the sphere inscribed in the clearance formed between the π-conjugated metal complex molecules are used as the supporting salt. FIG. 3B is a schematic representation of a complex molecule/substrate interface when cations having an ion radius equal to or larger than that of the sphere inscribed in the clearance formed between the π-conjugated metal complex molecules are used as the supporting salt. Reference numeral 3000 represents a substrate, and the π-conjugated metal complex molecules 3010 are connected thereto via π-conjugated molecular structures 3020 and are disposed in an aqueous electrolyte 3030.

When cations 3050 having an ion radius less than that of the sphere inscribed in the clearance formed between the π-conjugated metal complex molecules are used as the supporting salt, the cations can penetrate between the complex molecules and substrate. Therefore, the electric potential applied to the substrate is saturated in close proximity to the electrode and an electric potential profile, such as represented by the reference numeral 3060, is created, whereby the electric potential applied to the π-conjugated metal complex molecules is screened. This is believed to be why the electron transfer (redox reaction) of the π-conjugated metal complex molecules cannot be observed. On the other hand, when cations 3040 having an ion radius equal to or larger than that of the sphere inscribed in the clearance formed between the π-conjugated metal complex molecules are used as the electrolyte, the cations cannot penetrate between the complex molecules and substrate. As a result, the electric potential applied to the substrate is applied to the π-conjugated metal complex molecules and, therefore, the electron transfer (redox reaction) of the π-conjugated metal complex molecules can be observed.

Examples of cations derived from organic compounds that can be used in accordance with the present invention include 1-ethyl-3-methylimidazolium ion (0.239 nm), tetraethylammonium ion (0.4 nm), tetrapropylammonium ion (0.452 nm), and tetrabutylammonium ion (0.494 nm). Combinations of anions and cations having a large ion radius are often used as substances constituting ionic liquids, and they may also be used as solvents serving as supporting salts. Examples of properties that are necessary for the supporting salt include high solubility and sufficient stability at an electrode operation potential.

The ion radius can be established using reference values. Ion radii of metals are described in R. D. Shanon. Acta Crystallographica A, 1976, vol. 32, pp. 751. The following values are presented therein: $Na^+$ (0.102 nm), $K^+$ (0.138 nm), $Cs^+$ (0.167 nm) (all the values presented herein relate to a six-coordinate complex). As for organic ions, for example, ammonium ions are described in R. Wachter, K. Riederer. Pure and Applied Chemistry, 1981, vol. 53, pp. 1301, and the following values are presented therein: tetraethylammonium ion (0.4 nm), tetrapropylammonium ion (0.452 nm), and tetrabutylammonium ion (0.494 nm). Further, imidazolium ions are described in N. E. Heimer, J. S. Wilkes, P. G. Wahlbeck, W. R. Carper. The Journal of Physical Chemistry, A 2006, vol. 110, pp. 868, and 1-ethyl-3-methylimidazolium ion (0.239 nm) is described.

The π-conjugated metal complex molecules immobilized substrate in accordance with the present invention can be used in combination with aqueous electrolytes in devices for detecting substances by observing variations in the electrochemical response of π-conjugated metal complex molecules, or in devices that take out the energy generated by an electrochemical reaction as electrical energy.

A large number of biological materials may be present in various aqueous solutions, such as bodily fluids. Biological materials, such as DNA or proteins, coagulate or undergo modifications in environments other than aqueous solutions and, therefore, often cannot maintain their structures and demonstrate their functions. In accordance with the present invention, the electron transfer (redox reaction) of the π-conjugated metal complex molecules can be easily observed even when the π-conjugated metal complex immobilized substrate is used in an aqueous electrolyte. Therefore, the electrochemical device in accordance with the present invention can be used as a biological material detection device and/or a device for generating energy using a biological material as fuel. The biological material as used herein refers to a substance present in a living body. Specific examples of biological materials include proteins, nucleic acids, sugars, and alcohols.

EXAMPLES

The present invention is described below in greater detail with reference to specific examples. However, the invention is not limited to these examples. Synthesis of the metal complex ligands for immobilization on an electrode, preparation of π-conjugated metal complex immobilized electrodes, and electrochemical measurements were performed as follows.

Example 1

Figure 4:
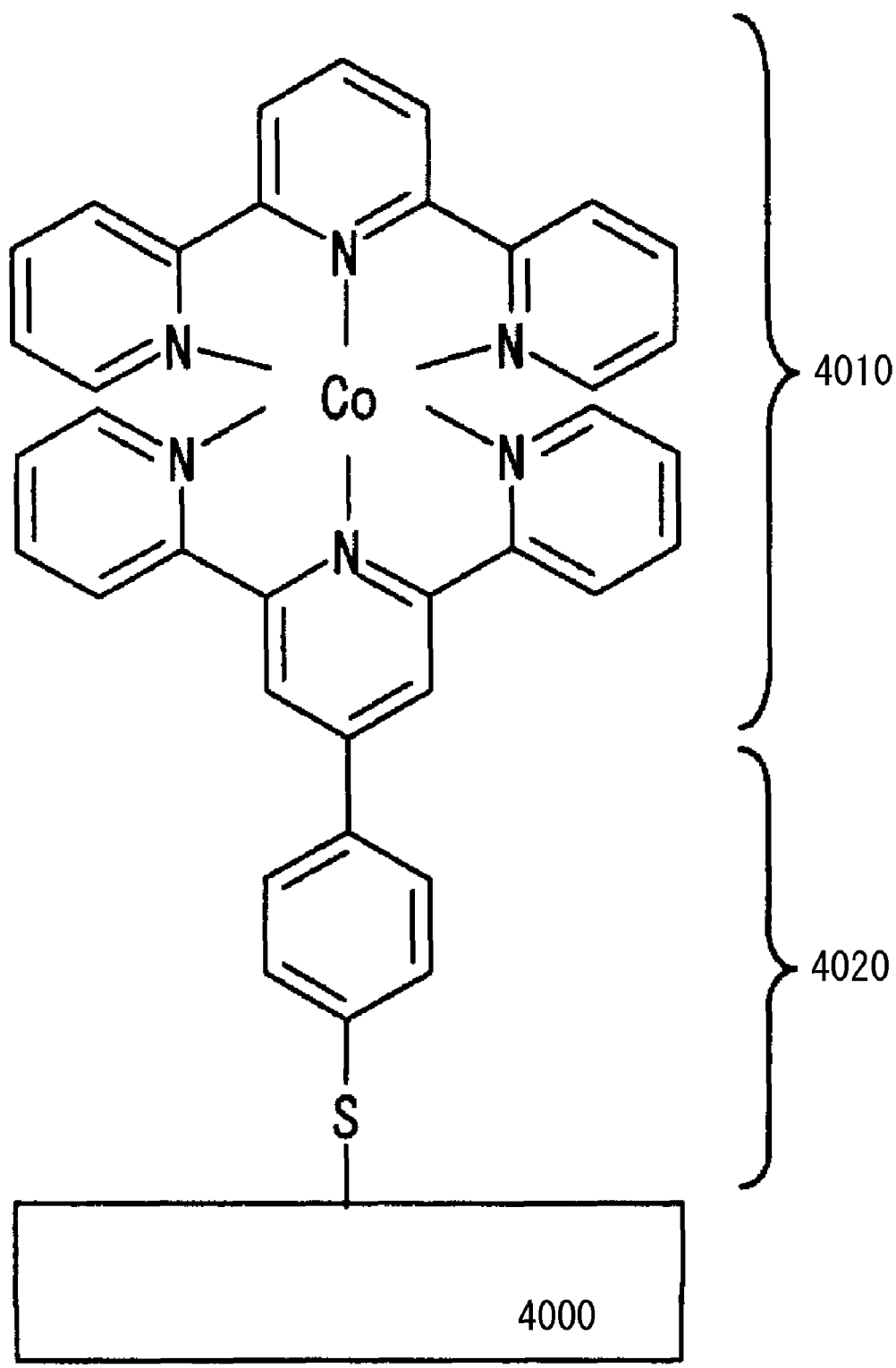
FIG. 4 is a conceptual view of a π-conjugated metal complex immobilized substrate formed in Example 1.

FIG. 4 is a conceptual view of a π-conjugated metal complex immobilized substrate formed in Example 1. In the figure, reference numeral 4000 represents a glass substrate with a vapor-deposited gold surface. A π-conjugated metal complex molecule (cobalt terpyridine complex) 4010 is immobilized on the substrate via a π-conjugated molecular structure 4020 (phenylthiol).

Synthesis of Metal Complex Ligand for Immobilization on Electrode

A method for synthesizing the complex ligand represented by formula (i) is described below:

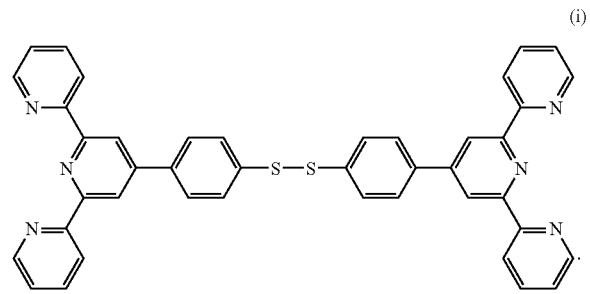

(i)

An ethanol solution containing equimolar amounts of 2-acetylpyridine and 4-methylthiobenzaldehyde was prepared. A 1.5 M aqueous solution of sodium hydroxide having a volume that was one-half that of the ethanol solution was added thereto and a reaction was conducted. The product of the reaction was filtered, washed with water and then methanol, and dried to obtain intermediate product 1.

A total of 0.1 mL of 2-acetylpyridine was added under a nitrogen atmosphere to a tetrahydrofuran solution of potassium-tert-butoxide and stirring was performed at room temperature. A total of 0.16 g of the intermediate product 1 was added and the reaction was performed at room temperature. Then, an excess amount of ammonium acetate was added and refluxing was performed. The solution was then vacuum-distilled and the product was washed with water and reprecipitated with methanol from chloroform, thereby producing an intermediate product 2 represented by formula (i).

A tenfold molar equivalent of sodium ethane thiolate was added under a nitrogen atmosphere to a DMF solution of the intermediate product 2. After refluxing, the reaction liquid was vacuum-distilled, an excess amount of aqueous solution of ammonium chloride was added, and the precipitate was recovered and then recrystallized with methanol to produce a compound represented by Formula 1. Identification was performed by $^1$H, $^{13}$H NMR and mass spectroscopy. A mass signal at 681 corresponding to the compound represented by Formula 1 was observed in the mass spectroscopy.

Preparation of π-Conjugated Metal Complex Immobilized Substrate

Commercial slide glass was ultrasonically washed in 2-propanol and acetone and dried under a nitrogen flow. Titanium/gold were then vapor deposited to a thickness of $^{20}/_{200}$ nm to prepare a conductive substrate. The substrate was cut, immersed for 20 min in a solution containing aqueous hydrogen peroxide and concentrated sulfuric acid at a weight ratio of 3/7, washed with water, and dried in a nitrogen flow.

The substrate was immersed in a chloroform solution of the ligand represented by formula (i), washed, and dried under a nitrogen flow. The substrate was then immersed in an ethanol solution of cobalt (II) borofluoride, washed, and dried under a nitrogen flow. Then, the substrate was immersed in an ethanol solution of 2,2':6',2''-terpyridine, washed, and dried under a nitrogen flow.

The adsorption density of π-conjugated metal complex molecules in the prepared π-conjugated metal complex immobilized substrate is estimated to be $1.25 \times 10^{-10}$ mol cm$^{-2}$, and the molecular radius of the π-conjugated metal complex molecule is estimated to be 0.58 nm. Therefore, the radius of the sphere inscribed in the clearance formed between the π-conjugated metal complex molecules is 0.239 nm.

Electrochemical Measurements

Figure 8:
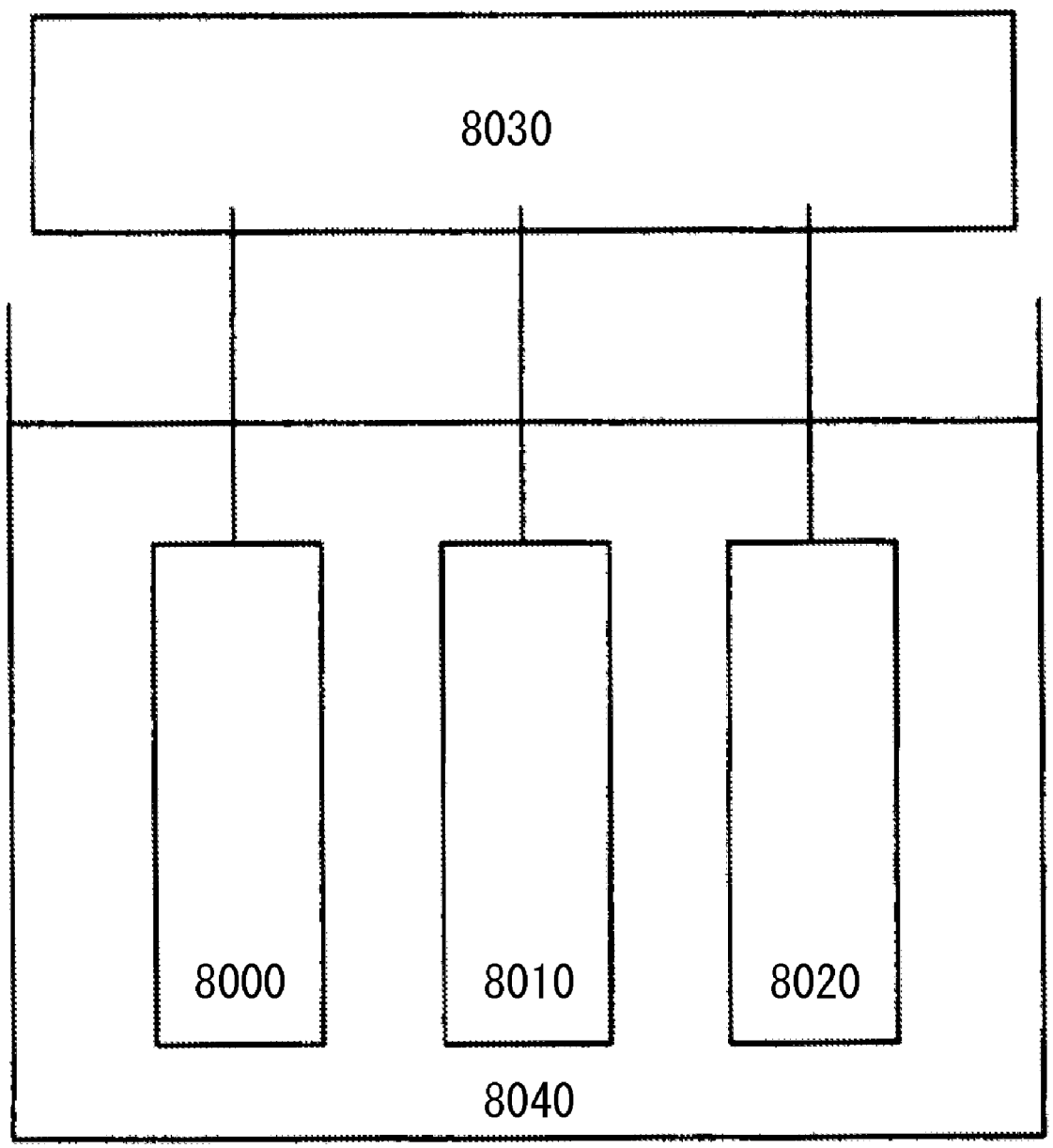
FIG. 8 is diagram of a three-electrode cell using the π-conjugated metal complex immobilized substrate.

A device using the π-conjugated metal complex immobilized substrate and the measurement method is described below. As shown in FIG. 8, the prepared π-conjugated metal complex immobilized substrate was used as working electrode 8000, a silver/silver chloride (NaCl) electrode was used as a reference electrode 8010, platinum was used as a counter electrode 8020, and cyclic voltammogram (CV) measurements were performed. The three electrodes were connected to a potentiostat 8030 and measurements were taken at a scan rate of 100 mVs$^{-1}$. The measurement temperature was about 25° C. A 0.1M aqueous solution of 1-ethyl-3-methylimidazolium hexafluorophosphate (EMIPF$_6$) was used as an electrolytic solution 8040 using a supporting salt composed of cations having a large ion radius in accordance with the present invention. The ion radius of the electrolyte cations was 0.239 nm and the ion radius of the anions was 0.254 nm. Further, a 0.1 M phosphate buffer (Na salt) with a pH of 7.0 (cation radius of 0.102 nm, anion radius of 0.238 nm) was used as a comparative electrolytic solution.

Figure 5:
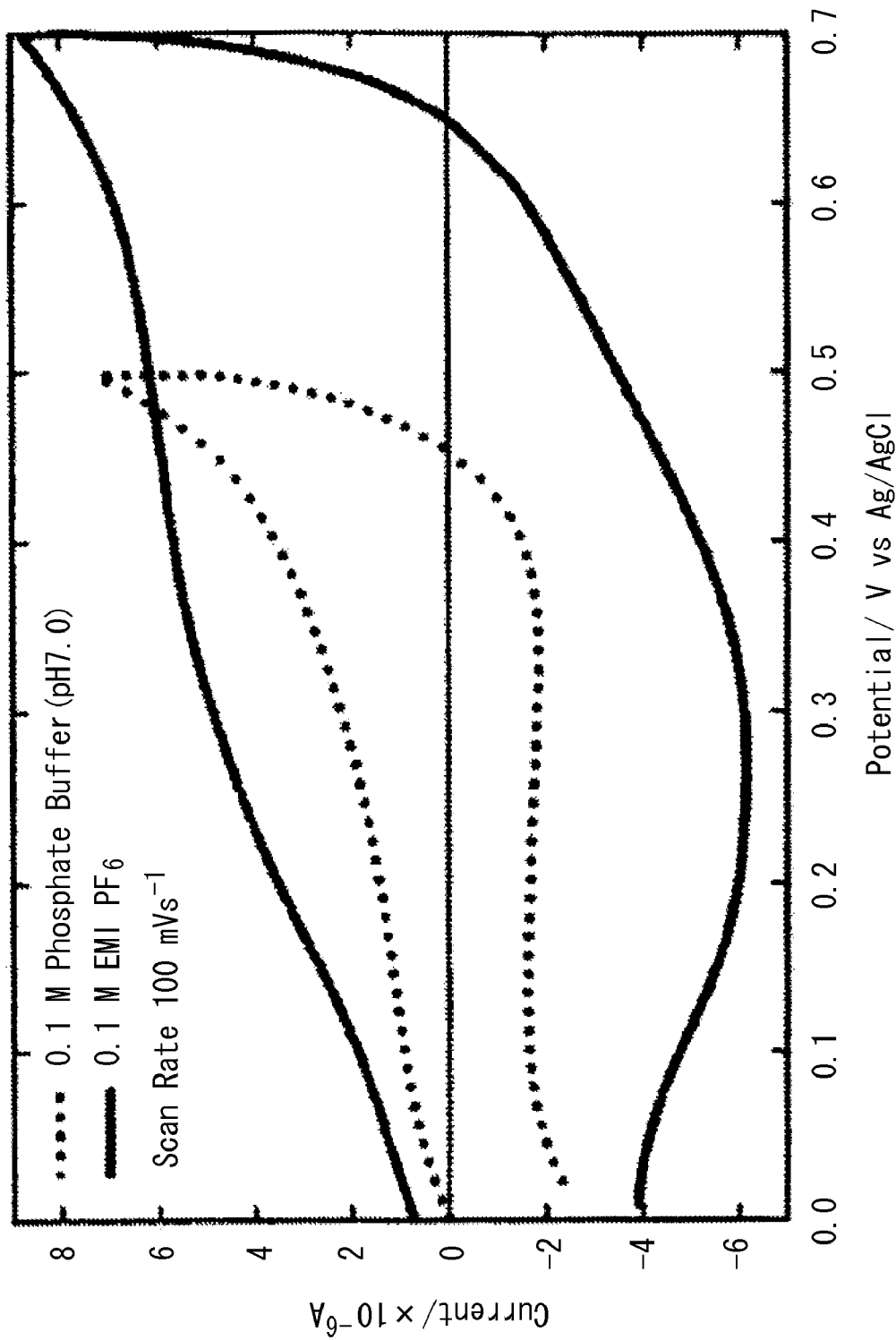
FIG. 5 is a plot based on a cyclic voltammogram measurement in each electrolyte (Example 1).

In FIG. 5, a CV obtained using EMIPF$_6$ as an electrolyte is represented by solid lines and a CV obtained by using the phosphate buffer as an electrolyte is represented by dotted lines. As shown in FIG. 5, a current caused by oxidation and reduction of cobalt was observed close to 0.3 V from the CV obtained by using an electrolytic solution containing EMIPF$_6$ as a supporting salt. By contrast, a current caused by oxidation and reduction of cobalt was not observed from the CV obtained by using the phosphate buffer as an electrolytic solution.

Example 2

Figure 6:
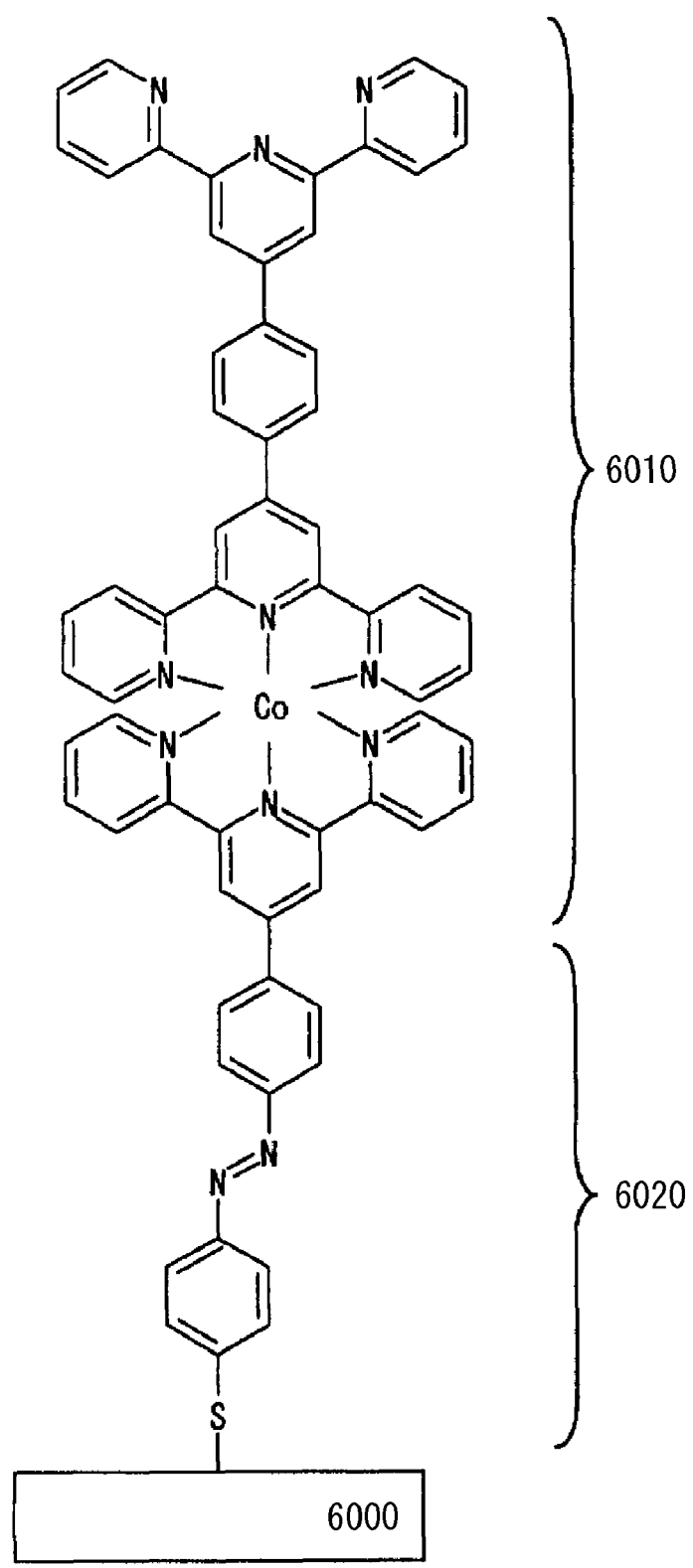
FIG. 6 is a conceptual view of a π-conjugated metal complex immobilized substrate formed in Example 2.

FIG. 6 is a conceptual view of a π-conjugated metal complex immobilized substrate formed in Example 2. In the figure, reference numeral 6000 represents a glass substrate with a vapor-deposited gold surface. A π-conjugated metal complex molecule (cobalt terpyridine complex) 6010 is immobilized on the substrate via a π-conjugated molecular structure 6020 (azobenzene site).

Synthesis of Metal Complex Ligand for Immobilization on Electrode

A method for synthesizing the complex ligand represented by formula (ii) is described below:

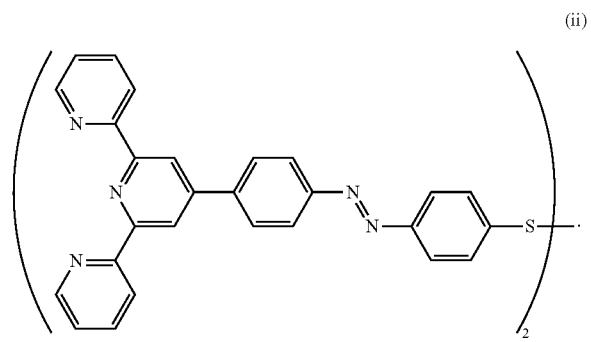

(ii)

One equivalent of 4-aminobenzaldehyde, two equivalents of 2-acetylpyridine, ten equivalents ammonium acetate, and acetamide were combined, and refluxing was performed for 3 hours in an air atmosphere. The reaction liquid was cooled in air, 500 g of an aqueous solution of sodium hydroxide was added, and refluxing was performed. Then, the reaction liquid was cooled in air, and an oily solid body was washed with water. The residue was dissolved in hot hydrobromic acid, the obtained dark-brown precipitate was filtered, 300 mL of water was added, and basicity was obtained with sodium hydrogen carbonate. The obtained solid body was extracted with chloroform and recrystallized with a column to obtain 4'-(4-anilino)-2,2':6',2"-terpyridine.

Then, 4'-(4-anilino)-2,2':6',2"-terpyridine and ammonium chloride were added to an aqueous solvent, a zinc powder was added under intensive stirring with a stirrer, and the reaction was conducted for 20 minutes. The reaction liquid was filtered and poured onto a large amount of ground ice, followed by the addition of concentrated sulfuric acid. Sodium dichromate was added to the solution, the solution was stirred, and the precipitate thus produced was collected and washed with water and dried to yield 4'-(4-nitrosobenzene)-2,2':6',2"-terpyridine.

The 4'-(4-nitrosobenzene)-2,2':6',2"-terpyridine was added to acetic acid. Then, 4,4'-dithioaniline was added and the components were stirred at room temperature. Water and sodium carbonate were added for neutralization, and the product was extracted with 150 mL of chloroform. A column using alumina as a filler was used and the obtained solution was distilled under reduced pressure and dried to produce the complex ligand represented by formula (ii).

Preparation of π-Conjugated Metal Complex Immobilized Substrate

Commercial slide glass was ultrasonically washed in 2-propanol and acetone and dried under a nitrogen flow. Titanium/gold were then vapor-deposited to a thickness of 20/200 nm to prepare a conductive substrate. The substrate was cut, immersed for 20 minutes in a solution containing aqueous hydrogen peroxide and concentrated sulfuric acid at a mass ratio of 3/7, washed with water, and dried in a nitrogen flow.

The substrate was immersed in a chloroform solution of the ligand represented by formula (ii), washed, and dried under a nitrogen flow. The substrate was then immersed in an ethanol solution of cobalt (II) borofluoride, washed, and dried under a nitrogen flow. Then, the substrate was immersed in a chloroform solution of 4',4''''-(1,4-Phenylene)bis(2,2':6',2''-terpyridine), washed, and dried under a nitrogen flow.

Electrochemical Measurements

A device using the π-conjugated metal complex immobilized substrate and the measurement method are described below. As in Example 1, the device shown in FIG. 8 was used. The prepared π-conjugated metal complex immobilized substrate was used as a working electrode 8000, a silver/silver chloride (NaCl) electrode was used as a reference electrode 8010, platinum was used as a counter electrode 8020, and cyclic voltammogram (CV) measurements were performed. The three electrodes were connected to a potentiostat 8030 and measurements were taken at a scan rate of 100 mVs$^{-1}$. The measurement temperature was about 25° C. A 0.1M aqueous solution of 1-ethyl-3-methylimidazolium hexafluorophosphate (EMIPF$_6$) was used as an electrolytic solution 8040 using a supporting salt composed of cations having a large ion radius in accordance with the present invention. The ion radius of the electrolyte cations was 0.239 nm and the ion radius of anions was 0.254 nm. Further, a 0.1 M phosphate buffer (Na salt) with a pH of 7.0 (cation radius of 0.102 nm, anion radius of 0.238 nm) was used as a comparative electrolytic solution.

Figure 7:
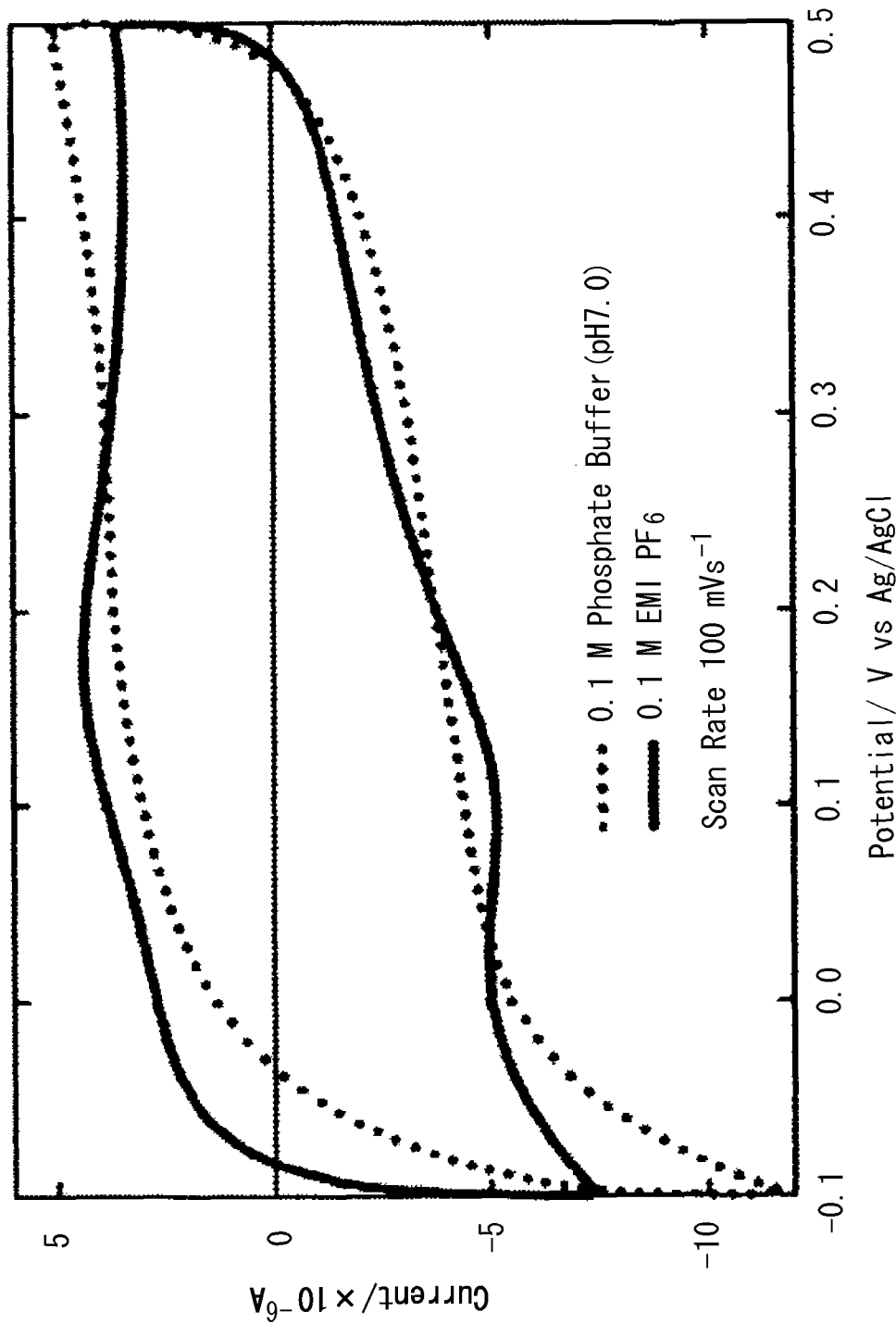
FIG. 7 is a plot based on a cyclic voltammogram measurement in each electrolyte (Example 2).

In FIG. 7, a CV obtained by using the EMIPF$_6$ as an electrolyte is represented by solid lines and a CV obtained by using the phosphate buffer as an electrolyte is represented by dotted lines. As shown in FIG. 7, a current caused by oxidation and reduction of cobalt was observed close to 0.13 V from the CV obtained by using an electrolytic solution containing EMIPF$_6$ as a supporting salt. By contrast, a current caused by oxidation and reduction of cobalt was not observed from the CV obtained by using the phosphate buffer as an electrolytic solution.

Analysis of Results in Examples

In the device using the π-conjugated metal complex immobilized substrate in accordance with the present invention, cations having an ion radius larger than that of the supporting salts that are typically employed in aqueous electrolytes is used as the electrolyte. As a result, the electron transfer (redox reaction) of the π-conjugated metal complex molecules of the π-conjugated metal complex immobilized substrate, in which the π-conjugated metal complex molecules are connected directly of via a π-conjugated molecular structure to the substrate, can be observed in the aqueous electrolyte. The following results are obtained with this device.

1. A device demonstrating high electron transfer inherent to a π-conjugated molecular structure can be produced.

In the conventional substrates with immobilized π-conjugated metal complex molecules that have been used in aqueous electrolytes, the molecules are connected to the electrode via a molecular structure that is not π-conjugated. In such a structure, movement is allowed due to the flexibility of the non-π-conjugated molecules. This is believed to be the reason why the inner region (closer to electrode) of the supporting salt can be reached or the penetration of the supporting electrolyte can be prevented by the packing of the alkyl chains induced by intermolecular forces. This is apparently the reason why oxidation and reduction of π-conjugated metal complex molecules is observed even in an aqueous electrolyte. However, in a structure in which the complex and the substrate are connected via a non-π-conjugated molecular structure, excellent electron transfer ability of π-conjugated molecular structures cannot be utilized. In the examples of the present invention, cations with an ion radius larger than that of most supporting salts that are generally employed as aqueous electrolytes were used as the electrolyte, whereby the cations were prevented from penetrating between the π-conjugated metal complex molecule and substrate. As a result, excellent electron transfer ability of π-conjugated molecular structures can be utilized even in aqueous electrolytes.

Where the electron transfer from the complex to the substrate is accelerated, for example, in sensors with a high response rate of systems in which the electron transfer from an enzyme to a substrate (complex) on the enzyme electrode is a speed-defining stage, the turnover number of the enzyme can be increased. As a result, a sensor with a wide detectable concentration range, an ultrasmall sensor, or an energy device, such as a battery with a large current (output), can be produced.

2. A large number of biological materials can be used.

A large number of biological materials are present in many aqueous solutions, such as body fluids. For this reason, biological materials, such as DNA or proteins, coagulate or undergo modifications in environments other than aqueous solutions. Therefore, they often cannot maintain their structures or properties.

In the π-conjugated metal complex immobilized substrate in accordance with the present invention, the electron transfer (redox reaction) of π-conjugated metal complex molecules on a π-conjugated metal complex immobilized substrate, in which the π-conjugated metal complex molecules are connected to the substrate directly or via a π-conjugated molecular structure, can be observed in an aqueous electrolyte. Therefore, biological materials maintain their structures and functions.

With the above-described advantageous electrochemical device in accordance with the present invention, the electron transfer (redox reaction) of π-conjugated metal complex molecules immobilized on a conductive substrate can be observed in an aqueous electrolyte.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-190705, filed Jul. 23, 2007, which is hereby incorporated by reference herein in its entirety.

What is claimed is:

1. An electrochemical device comprising:
   a π-conjugated metal complex immobilized substrate in which π-conjugated metal complex molecules are immobilized on a conductive substrate directly or via a π-conjugated molecular structure; and
   an aqueous electrolyte comprising cations with an ion radius that is not smaller than a radius of a sphere inscribed in a clearance between the π-conjugated metal complex molecules,
   wherein the device utilizes a redox reaction of the π-conjugated metal complex molecules in the aqueous electrolyte, and
   wherein the radius of the sphere inscribed in the clearance formed between the π-conjugated metal complex molecules is represented by Equation (1):

$$A = \frac{1}{\sqrt{2 \times 10^4 G N_A}} - R, \quad (1)$$

where A is the radius of the sphere inscribed in the clearance formed between the π-conjugated metal complex molecules, G is an adsorption density (mol cm$^{-2}$) of the π-conjugated metal complex molecules, $N_A$ is Avogadro's number, and R is a molecular radius (m) of a π-conjugated metal complex molecule.

2. The electrochemical device according to claim 1, wherein a cation having the ion radius r is derived from an organic compound.

* * * * *